United States Patent [19]

Albillos et al.

[11] Patent Number: 5,739,384
[45] Date of Patent: Apr. 14, 1998

[54] INDUSTRIAL PROCESS TO MANUFACTURE AROMATIC CARBOXYLIC ACIDS

[75] Inventors: Miguel Angel Melgosa Albillos, Algeciras; Jorge Molina Marsans, Las Rozas; Lorenzo Ortega Calvo, La Linea, all of Spain

[73] Assignee: Intercontinental Quimica, S.A. (Interquisa), Madrid, Spain

[21] Appl. No.: 717,016

[22] Filed: Sep. 20, 1996

[30] Foreign Application Priority Data

Sep. 21, 1995 [ES] Spain ............................ 9501832

[51] Int. Cl.$^6$ ............................................. C07C 51/265
[52] U.S. Cl. ............................................. 562/414
[58] Field of Search ................................... 562/414

[56] References Cited

U.S. PATENT DOCUMENTS

| 2,245,528 | 6/1941 | Loder . |
| 2,833,816 | 5/1958 | Saffer et al. . |
| 2,997,500 | 8/1961 | Moscrip et al. . |
| 3,069,462 | 12/1962 | Saffer et al. . |
| 3,733,354 | 5/1973 | Cassar et al. . |
| 3,920,735 | 11/1975 | Wampfler et al. . |
| 4,391,985 | 7/1983 | Hook et al. . |
| 4,777,287 | 10/1988 | Zeidlin et al. . |
| 4,835,307 | 5/1989 | Lindhal et al. . |
| 5,453,538 | 9/1995 | Broeker et al. . |

FOREIGN PATENT DOCUMENTS

| 026507 | 4/1981 | European Pat. Off. . |
| 257788 | 3/1988 | European Pat. Off. . |
| 341813 | 11/1989 | European Pat. Off. . |
| 343991 | 11/1989 | European Pat. Off. . |
| 349189 | 1/1990 | European Pat. Off. . |
| 361788 | 4/1990 | European Pat. Off. . |
| 341942 | 8/1961 | Spain . |
| 384609 | 10/1964 | Spain . |
| 402294 | 4/1972 | Spain . |
| 404182 | 6/1972 | Spain . |
| 426529 | 1/1976 | Spain . |
| 461021 | 7/1977 | Spain . |
| 494563 | 8/1980 | Spain . |
| 548283 | 10/1985 | Spain . |
| 549929 | 12/1985 | Spain . |
| 1144687 | 3/1969 | United Kingdom . |
| 1155589 | 6/1969 | United Kingdom . |
| 1389478 | 4/1975 | United Kingdom . |
| 1577544 | 10/1980 | United Kingdom . |

OTHER PUBLICATIONS

Westerterp, K.R. (1984) In: Chemical reactor design and operation, John Wiley, pp.597–613.
Westerterp et al. (1983) Chem. Engineer. Sci. 38:1331–40.

*Primary Examiner*—Samuel Barts
*Attorney, Agent, or Firm*—Klauber & Jackson

[57] ABSTRACT

The process that involves liquid phase catalytic oxidation of a mono- or poly-substituted alkyl aromatic compound comprises: (i) microdispersion of the air in the reactor at a pressure between 15 and 25 atmospheres and at a rate between 200 and 500 kg/sec.m$^2$; and (ii) recycling the catalyst by evaporation of the purge that contains it and leaching the resulting paste with distilled water at 20°–40° C. to dissolve the catalyst separating it from the rest of the components.

Aromatic carboxylic acids are basic products used in a large number of industrial fields.

5 Claims, 2 Drawing Sheets

INDUSTRIAL PROCESS TO MANUFACTURE AROMATIC CARBOXYLIC ACIDS

TECHNICAL FIELD OF THE INVENTION

This invention refers to the industrial manufacturing of aromatic carboxylic acids such as benzoic acid, terephthalic acid, trimesic acid, 2,6-dicarboxynaphthalene, etc., by liquid phase catalytic oxidation, of the corresponding alkyl-substituted hydrocarbons, the oxidizing agent being the oxygen of air and the customary solvent being an aliphatic carboxylic acid, such as acetic acid.

PRIOR ART OF THE INVENTION

Liquid phase oxidation of aromatic alkyl compounds is a highly exothermic reaction that has been known for many years.

In June 1941, D. J. Loder of E. I. Du Pont de Nemours, patented a process for "Catalytic oxidation of alkyl substituted aromatic compounds" (U.S. Pat. No. 2,445,528) of 10 Jun. 1941) in liquid phase, pressurized, to produce benzoic acid and phthalic acids by oxidation of toluene and xylene mixtures. The oxidizing agent had to be a gas containing oxygen (such as air), the solvent an organic acid (such as acetic acid), the temperature was between 130° and 250° C. and the pressure was between 2 and 100 atmospheres, the catalysts were soluble salts (mainly acetates) of polyvalent metals, preferably cobalt and manganese. Finally, D. J. Loder proposes several organic substances, preferably aldehydes and ketones as promoters. Saffer, Bayside and Barker (Mid-Century Corp.): Preparation of polycarboxylic acid (U.S. Pat. No. 2,883,816, 6 May 1958) describes the liquid phase oxidation process, providing as a novelty, over the previous patent the use of ionic form bromine compounds (hydrobromic acid or bromides) or in organic form (tetrabromoethane), as promoters of the catalytic reaction, instead of the aldehydes and ketones proposed by Loder. The patent thoroughly describes 49 examples of oxidation, among which no. 1 (oxidation of p-xylene to produce terephthalic acid) and no. 7 (oxidation of m-xylene to produce isophthalic acid) stand out. Zeitlung and McQuilling (Amoco Corp.): "Process for the continuous production of aromatic carboxylic acid" (Spanish patent 548,283, 28 Oct. 1985) describe a process for the manufacture of an aromatic carboxylic acid, following the guidelines of the two previous patents, but specifying a bit more the operating conditions (the temperature of the reactor is between 120° and 230° C. and the pressure is between 0 and 35 Kg/cm$^2$.) Besides the heat generated by the reaction is dissipated by the vaporization of the solvent (a mixture of acetic acid and water). The vaporized solvent is condensed in a heat exchanger, returning the condensate to the oxidation reactor as reflux.

Abrams (Amoco Corp.) "Process for the continuous production of aromatic carboxylic acid" (European patent 87306454.7 of 21 Jul. 1987) describes a method for the continuous production of an aromatic carboxylic acid in a pressurized reactor in liquid phase, the oxidizing agent being a gas that contains oxygen, such as air. The heat produced by the oxidation is eliminated from the reactor by the vaporization of the solvent and of the water produced by the reaction. In this case, the vapors are partially condensed in a first heat exchanger outside the reactor returning the condensate, as reflux to the top part of the reactor. The uncondensed gaseous phase passes to a second condenser where, by cooling, a second part (richer in water) is condensed, at a lower temperature which in part is reintroduced through a pipe outside the bottom part of the reactor. Finally the uncondensed gaseous phase is introduced in a third cooler whose condensed product is recirculated, in part, to the oxidation reactor, mixed with the liquid feed to the same. This system makes it possible to maintain a suitable concentration of water in the reacting mass.

Lee (Amoco Corp.): "Reactor and process for the oxidation of alkyl aromatic compounds to aromatic carboxylic acids" (European patent 89302555.1 of 15 Mar. 1989) describes the geometry of a continuous agitated reactor, designed for the oxidation of alkyl-substituted aromatic compounds. The agitator is comprised of a vertical shaft, centered with regard to the container and provided with two impellers. The bottom impeller generates an axial flow (slanted blades), while the top impeller generates a radial flow (flat vertical blades). The reactor has vertical screens near the wall of the container which is cylindrical-vertical. Finally, the reactor also has four equidistant air intakes located halfway between the bottom of the reactor and the bottom impeller of the agitator.

Hundley (Amoco Corp.) "Process for production of aromatic polycarboxylic acids" (European patent 89305316.5 of 25 May 1989) comments that the lower the reaction temperature and, therefore, the pressure, the lesser the formation of coproducts and fewer losses of the solvent (oxidation of acetic acid); however, in an existing plant, the drop of pressure is limited by the reduction of the density of the vapors that causes an increase of rate of flow in the pipes, which causes a pressure drop that hampers the return of the condensate, by gravity, to the reactor. To remedy this situation, side extraction of the reaction liquid, to cool it in an outside cooler and to return it, through a pump, to the bottom part of the reactor is proposed.

From the previous patents and from the physicochemical study of the liquid phase oxidation reaction, of an alkyl aromatic hydrocarbon, using air as the oxidizing agent (Westerterm K. R.: "Chemical reactor design and operation" John Wiley, 1984), the following consequences are inferred:

a) The reaction is carried out in the center of the liquid phase, between the alkyl aromatic compound and the dissolved oxygen.

b) The dissolving of the oxygen is produced by bubbling air in the bottom area of the agitated reactor.

c) The lower the pressure at which the reaction is carried out, the less energy is required, to compress the air necessary for the same.

d) The pressure drop makes it necessary to lower the temperature of the reacting mass so that the temperature is always lower than its boiling point, at the operating pressure of the reactor, since if the reacting mass boils, it is totally degassed, hence the concentration of dissolved oxygen is nil and the reaction ceases.

e) Another advantage of working at a low pressure and, therefore, at a lower temperature is that the loss of solvent (acetic acid) is reduced considerably, due to the parallel oxidation reaction between the acetic acid and the dissolved oxygen.

From the above conditions it is inferred that it is interesting to carry out the oxidation reaction at the lowest possible pressure and temperature; however, the combined effect of both drops, leads to a considerable reduction of the reaction rate and, therefore, of production. In order to achieve a similar productivity, it is necessary to compensate the negative effect of the lower pressure and temperature, by increasing, on the one hand, the solution rate of the oxygen and, on the other hand, the rate of the chemical reaction itself, between the dissolved oxygen and the aromatic hydrocarbon. In this way, reaction rates similar to those attained at higher pressures and temperatures can be achieved.

DETAILED DESCRIPTION OF THE INVENTION

As indicated in its title, the present invention refers to an industrial process to manufacture aromatic carboxylic acids.

As it has been commented on above, the industrial production of aromatic carboxylic acids is based on liquid phase catalytic oxidation of the corresponding alkyl-substituted hydrocarbons using the oxygen of air as the oxidizing agent.

Now then, the main aim of the present invention lies on the attainment of the oxidation reaction at the lowest possible pressure and temperature, without considerably reducing the reaction rate and, therefore, of the production process.

The present invention achieves the cited aim by introducing two new essential aspects in the process, that is to say: microdispersion of the air and recovery of the catalyst with subsequent recycling.

Each one of these aspects will be analyzed in further detail in the following paragraphs.

The oxidation reactors for the obtainment of aromatic carboxylic acids comprise an agitated reactor in which an excess of air, which is dispersed by the turbulence produced by the impellers of the agitator, is bubbled. It is obvious that the smaller the air bubbles, the larger the specific surface of the interphase thereof and the faster the rate of the oxygen transference process, from the inside of the air bubble to the center of the reacting mass. Normally, in an industrial reactor, the air is introduced through two or four pipes, symmetrically distributed and with a diameter between 50 and 150 mm, depending on the size of the reactor, or in other words, on the production of the plant. These pipes did not have up until now any device to increase the air dispersion.

In accordance with the present invention, the two or four pipes are closed by a sintered titanium cover (grade 2 or 3) in the manner of a filtering plate, with some pores whose diameter must be between 20 and 60 microns, in such a way that by bubbling, through each pipe, air at a pressure between 15 and 25 atmospheres and at a mass rate between 200 and 500 kg/sec.m$^2$, the pressure drop, through the plate is lower than 0.5 atmospheres. With this device (FIG. 1), by bubbling air, with the agitator in operation, the air comes out very finely divided, increasing the rate of the physical process of the transfer of matter.

In order to increase the rate of the chemical process, in a proportion similar to the increase undergone by the rate of the physical oxygen transfer process, it is necessary to increase the concentration of the catalyst (cobalt and manganese acetates) and promoter (compound with bromine.) This increase, which is easy to achieve, by simply acting on the of the catalyst and promoter flow controllers, has two negative consequences that must be compensated for:

An increase of the cost of the operation, due to a higher consumption of catalyst.

An increase of the concentration of metals (manganese and cobalt) in the purge of mother liquors, necessary to maintain the optical properties of the manufactured product.

In order to avoid these inconveniences, the second aspect of the invention corresponding to the recovery and recycling of the catalyst has been developed.

The block diagram of the typical production of a carboxylic acid, such as terephthalic acid, from an alkyl aromatic hydrocarbon, such as p-xylene, is represented in FIG. 2. In this process, the recycling of the mother liquors (R) makes a purge (P) necessary in order to control the concentration of soluble byproducts and impurities, produced in the reactor and that, without the purge, would accumulate in the mother liquors, polluting the obtained product (D). With the purge, a bit of solvent, catalyst and promoter is inevitably lost, therefore it is necessary to replace the same. When in order to increase the reaction rate, the concentration of catalysts and promoter is increased, the loss of these products is proportionally increased, therefore it is necessary, due to economic reasons (cost of the catalysts) as well as due to ecological reasons (contamination of the effluent of the plant) to have a system to recover the catalysts from the purge and to recycle them to the process.

FIG. 3 represents the block diagram of the process developed to recover the catalysts in accordance with the patent of invention and that must function inserted between the purge (P) and the filler preparation container described in FIG. 2. The operation thereof is the following:

The purge (P) which is, for example, an aqueous solution of acetic acid saturated by the isomers of the carboxylic acid produced and the impurities thereof, passes to a rotary evaporator (6, FIG. 3), where, most of the water and acetic acid (stream L, FIG. 3) is lost by evaporation, the resulting concentrated solution is a paste, that flows with difficulty at the output temperature of the evaporator (between 150° and 250° C.), enters a leacher, where it is mixed with a flow of distilled water supercooled to a temperature between 10° and 25° C. The leacher is a stainless steel container provided with an agitator expressly designed to keep the carboxylic acid (terephthalic acid, isophthalic acid, etc.) in suspension, while the cobalt and manganese acetates, as well as the remaining acetic acid, are dissolved in water. It is necessary to supercool the distilled water provided to the leacher (stream S, FIG. 3) so that, upon mixing with the concentrated paste in the evaporator, a suspension at a temperature between 20° and 40° C. results. In this way, the cobalt and manganese acetates can dissolve perfectly, solubilizing a tiny amount of the organic acid and the impurities thereof. It is also necessary that the volume of the leaching container is such that the stay time of the suspension suffices so that all the catalyst dissolves. Finally, the aqueous suspension is sent to a centrifuge (8, FIG. 3) where the solid waste (M) is separated from the plant of the aqueous solution (N) that is recycled to the oxidation reactor, through the filler preparation container (1, FIG. 2).

An important parameter for the good operation of leaching is the ratio between the supercooled water and the solid to be suspended. It is necessary that the amount of water is the minimum needed to dissolve the acetates and to maintain the suspension. An excess of water facilitates the disintegration of the solid, but it recycles more impurities and hampers the reaction. A lack of water causes losses of catalyst. A good compromise is to keep the water/solid ratio at the entry of the leacher between 4 and 8 (kg/kg.)

1: Filler preparation

2: Oxidation

3: Crystallization

4: Solid-Liquid separation

5: Dryer

A: Aromatic alkyl

B: Catalysts and promoter

C: Solvent

D: Carboxylic acid

R: Recycling of mother liquors

P: Purge

Figure 1:
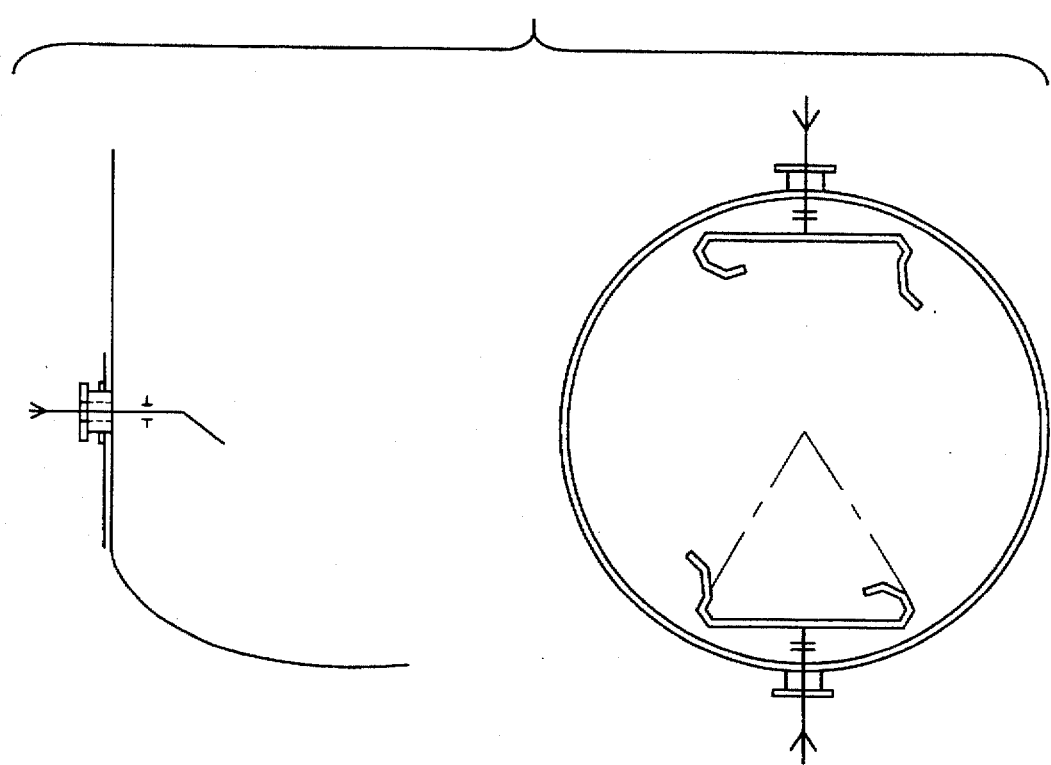
FIG. 1 represents the introduction device of the microdispersed air into the reactor, comprised of pipes whose ends are provided with a porous sintered titanium plate (grade 2 or 3).
Figure 2:
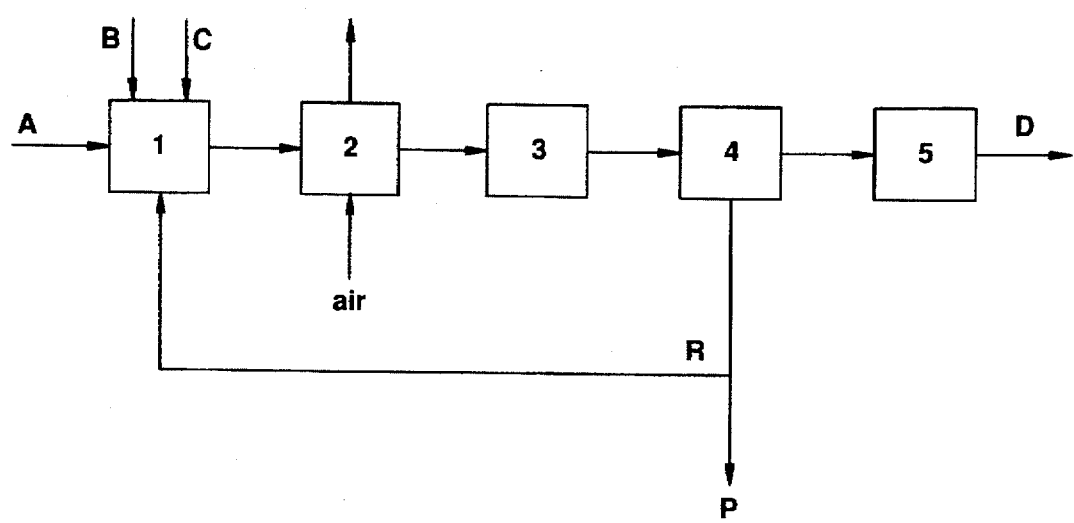
FIG. 2 represents the block diagrams of the typical production of a carboxylic acid from an alkyl aromatic hydrocarbon by oxidation with the oxygen of air. In the figure, the references have the following meaning.
Figure 3:
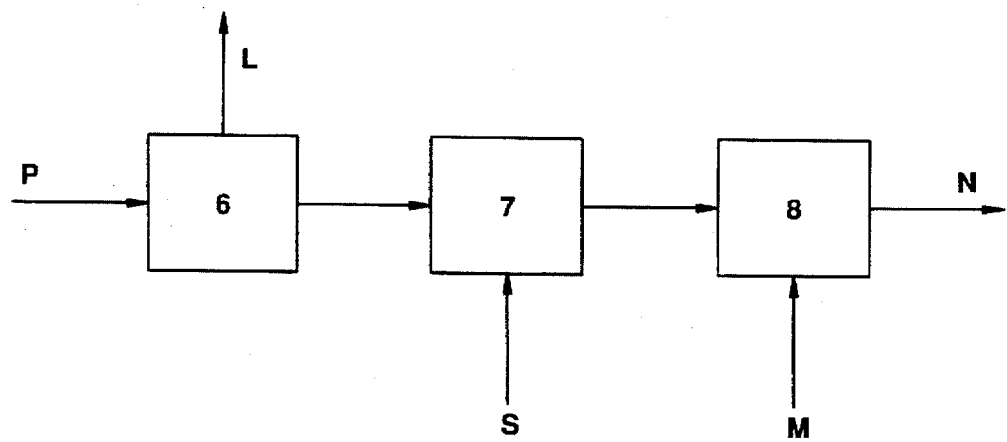

FIG. 3 represents the block diagram of the process developed by the present invention in order to recover the catalysts and it must function between the purge (P) and the filler preparation container of previous FIG. 2. In the figure, the references have the following meaning:

6: Evaporator

7: Leacher

8: Solid-Liquid separation

P: Purge

L: Solvent (acetic acid) to recovery

S: Distilled water

M: Solid waste, without catalyst

N: Aqueous solution with the catalyst

EMBODIMENTS OF THE INVENTION

The present invention is additionally illustrated by means of the following Example, which does not intend to be restrictive of the scope hereof.

EXAMPLE

A plant has two 50 m$^3$ oxidation reactors, designed to work at 25 atmospheres and at a temperature between 215° and 230° C. Working under these conditions, the plant production was 90,000 Tm/year of terephathalic acid. In order to improve the profitability of the plant, reducing costs, the condensation surface, the diameter of the gas pipes were increased and the compressor was modified, in order to be able to work at 16 atmospheres, which made it necessary to lower the temperature of the reactor down to a value between 190° and 200° C. Working under these conditions, with the same concentrations of catalyst, the production dropped considerably.

In order to recover the initial production, some sintered titanium filtering plates were installed, at the outlet of each one of the four air pipes of the reactor and the concentration of catalysts and promoter was increased between 25 and 40%. The plant production increased up to between 90 and 100,000 Tm/year. Comparably, a rotary evaporator, a 12 m$^3$ leacher, provided with an agitator comprised of two turbine type impellers, with flat blades, were installed, turning at an adjustable speed and, finally, a horizontal continuous settling tank. By means of this installation the consumption of catalysts dropped, maintaining the production and quality of the obtained product.

We claim:

1. A process for the manufacture of aromatic carboxylic acids by liquid phase oxidation of a mono- or poly- alkyl-substituted aromatic compound, oxidizable with molecular oxygen of air, in the presence of a catalyst soluble in a reacting mass comprised of said aromatic compound, cobalt and manganese acetates, and an organic or inorganic bromine that acts as promoter, the process being carried out in a reactor having at least one pipe for introducing air, comprising the steps of:

microdispersing the air that enters the reactor through said pipe, said pipe having a sintered titanium cover as a filtering plate with pores having a diameter between 20 and 60 microns, so that by bubbling air during said oxidation through the pipe at a pressure between 15 and 25 atmospheres and at a rate between 200 and 500 kb/sec m$^2$, produces a pressure drop through the filtering plate lower than 0.5 atmospheres, until obtaining a purge of an aqueous solution containing solvent acid, isomers of the carboxylic acid produced, catalysts and impurities and;

recycling the catalyst from said purge by passing said purge to a rotary evaporator where most of the water and the solvent acid are evaporated and a past is obtained, entering said paste into a leacher where it is mixed, at a temperature between 20° and 40° C. with a stream of distilled water in such a way that the carboxylic acid produced is kept in suspension in said leacher, whereas the catalyst and the solvent acid are dissolved, and finally separating the solid obtained from the aqueous solution which is recycled to the process.

2. A process according to claim 1, wherein said cover is sintered grade 2 titanium plate.

3. A process according to claim 1, wherein said cover is a sintered grade 3 titanium plate.

4. A process according to claim 1, wherein aromatic compound is a p-xylene and the carboxylic acid is terephthalic acid.

5. A process according to claim 1, wherein the said paste entering the leacher has a water/solid ratio of 4:8 kg/kg.

* * * * *